United States Patent [19]

Meyer et al.

[11] Patent Number: 4,772,271
[45] Date of Patent: Sep. 20, 1988

[54] PREFILLED SYRINGE

[75] Inventors: Gabriel Meyer; Ernst Howald, both of Vésenaz, Switzerland

[73] Assignee: Medicorp Holding S.A., Luxembourg, Luxembourg

[21] Appl. No.: 64,054

[22] PCT Filed: Aug. 8, 1986

[86] PCT No.: PCT/EP86/00470
§ 371 Date: Apr. 7, 1987
§ 102(e) Date: Apr. 7, 1987

[87] PCT Pub. No.: WO87/01042
PCT Pub. Date: Feb. 26, 1987

[30] Foreign Application Priority Data

Aug. 13, 1985 [FR] France .................. 85 12441

[51] Int. Cl.[4] ............................................. A61M 5/18
[52] U.S. Cl. .................................. 604/184; 604/200
[58] Field of Search ............ 604/187, 197, 200, 218, 604/232, 231, 184

[56] References Cited

U.S. PATENT DOCUMENTS 2,453,590 11/1948 Poux .
3,892,237 7/1975 Steiner ........................ 604/200
3,943,927 3/1976 Norgren .
4,091,812 5/1978 Helixon et al. .
4,227,528 10/1980 Wardlaw .

FOREIGN PATENT DOCUMENTS 0115931 8/1984 European Pat. Off. .
0150681 8/1985 European Pat. Off. .
2024089 8/1970 France .
2178019 11/1973 France .
2529086 12/1983 France .

Primary Examiner—John D. Yasko
Attorney, Agent, or Firm—Sandler & Greenblum

[57] ABSTRACT

The present invention relates to a prefilled syringe comprising a reservoir containing a single dose of medicine to be injected.

The principle elements of this syringe are the reservoir (10), a blocking element (12), a capsule (13) integral with this element, a needle (14), a needle-protector (15) and a cap (16). The cap (16), in place on the reservoir, makes it possible for the operator, by pressing on this cap to make the blocking element penetrate towards the interior of the reservoir a sufficient distance to cause the precise bubble removal of the syringe. To this end, the cap is connected to the capsule (13) by a base (36) comprising a zone of reduced resistance.

13 Claims, 2 Drawing Sheets

PREFILLED SYRINGE

The present invention relates to a prefilled syringe comprising an elongated reservoir open at one of its ends, containing a liquid, particularly liquid medicine to be injected, and an injection element movable with respect to this reservoir, this injection element comprising a blocking element at least partially engaged in the reservoir at its open end, and adapted to block the reservoir when the syringe is in a first position called a storage position and to assure the evacuation of the liquid when a syringe is in a second position called the injection position, as well as a capsule integral with this blocking element and mounted on the reservoir such that an end slice of this reservoir, adjacent to its opening, is engaged in this capsule.

Prefilled syringes of this type are adapted to be able to be stored during a period which can be relatively long. To this end, the blocking element comprises an elastomeric head which is strongly compressed within the neck of the reservoir. This blocking element further comprises elastic retention elements which have a tendency to retain it in its position and to prevent any displacement towards the interior of the reservoir. Finally, within this reservoir there exists an excess pressure which likewise opposes a force tending to prevent the penetration of the blocking element to the interior of the reservoir during the entire storage phase.

Consequently to bring the blocking element from its storage position in which it blocks in a sealed fashion the open end of the reservoir, towards its injection position in which it fills the double role of piston and valve to allow for the evacuation of the liquid medicine from the reservoir, it is necessary to exert a certain force adapted to overcome the initial inertia. If this force is exerted without control or restraint, a portion of the liquid contained in the reservoir may be ejected and lost. Being given that the volume of liquid medicine contained in the reservoir can correspond to a single dose, it is essential that this dose be injected in its entirety and that the loss of medication due to the phenomenon mentioned above be avoided, particularly when it is a question of doses of small volume.

The present invention proposes overcoming this problem by providing means making it possible to control in a precise fashion the passage of the syringe from its storage position to its injection position, and in particular to void the syringe of bubbles to render it absolutely ready for use.

To this end, the prefilled syringe according to the invention is characterized in that it is equipped with a cap fitted on top of the closed end of the elongated reservoir, and in that this cap is provided with removable linkage means to render this cap integral with the capsule, when the syringe is in its first position, and support means to allow for a relative limited displacement of the movable injection element and of the reservoir to bring the prefilled syringe from its first position into its second position.

According to a preferred embodiment, the said removable linkage means comprise a base fixed to the capsule, this base being connected to the cap by a zone of lesser resistance.

The said base is preferably attached to an annular edge provided around the capsule adjacent to its end in which is engaged the open end of the reservoir.

The said annular edge provided around the capsule preferably forms two lateral maintenance wings of the syringe.

The said base is preferably welded by ultrasound to the annular edge.

The said support means preferably comprise at least one abutment adapted to cooperate with an edge of the cap and the distance between this abutment and this edge is preferably substantially equal to the said relative limited displacement of the movable injection element and of the reservoir. As a result, when these two elements are effectively displaced with respect to one another by this distance separating the abutment from the edge, the syringe is voided of air bubbles, i.e., brought into its use position.

According to a preferred embodiment, the said abutment comprises a surface of the said annular edge of the said base and the said edge of the cap which cooperates with this abutment is connected to this base by the zone of reduced resistance.

The base preferably has a generally cylindrical or conical shape whose smaller diameter is greater than the exterior diameter of the cap of generally cylindrical shape.

The zone of reduced resistance is preferably constituted by a closed annular element whose surface extends laterally towards the exterior of the cap.

According to another embodiment, the zone of reduced resistance is constituted by an assembly of flaps extending laterally towards the exterior of the cap.

This cap preferably comprises at least a support element provided on the interior and adapted to rest against the closed bottom of the reservoir.

The present invention will be better understood with reference to the description of one embodiment and the annexed drawings in which.

Figures 1, 2:
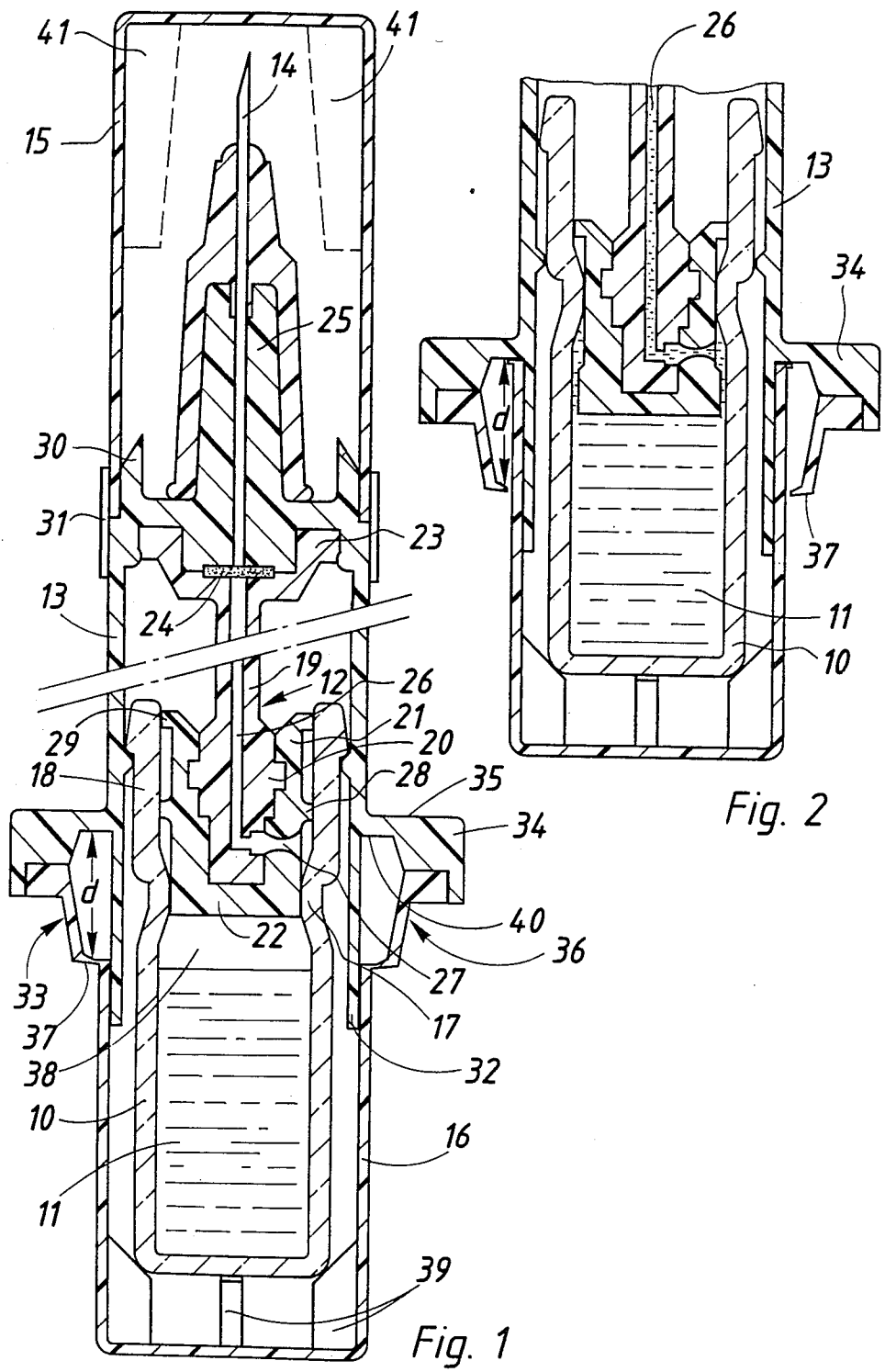
FIG. 1 illustrates a longitudinal cross-section of the syringe according to the invention, as it presents itself in its storage position.
FIG. 2 illustrates a partial view in longitudinal cross-section of the syringe according to FIG. 1 such as it presents itself at the moment when it is brought from its storage position to its injection position.

FIG. 1 shows by way of example a prefilled syringe having a single dose which essentially comprises a reservoir 10 containing a liquid medicine 11 to be injected, a blocking element 12, a capsule 13 integral with the blocking element 12, a needle 14, a needle protector 15 and a cap 16 serving to protect reservoir 10. One observes that by virtue of their shape, the needle protector 15 and the cap 16 cooperate with the capsule 13 to constitute a protective impregnable enclosure of the functional portions of the syringe. Reservoir 10 comprises a constricted portion 17 adjacnt to its neck 18 in which is engaged the blocking element 12. This latter is essentially composed of a piston shaft 19 of which a first enlarged end 20 serves as a stiffening element of an annular skirt 21 connected to a piston head 22 which effectively serves the role of blocking element of the reservoir during the storage period of the syringe. The second end 23 of the piston shaft is flared and comprises coupling elements to affix the said piston shaft coaxially to the interior of the capsule 13. A filter 24 is preferably mounted at the bottom of the capsule, in a sufficient seat, taken between the base of the piston shaft and the needle carrier tip 25 integral with the capsule. A central conduit composed of an axial arm 26 and a transverse arm 27 successively traverses the needle carrier tip, the piston shaft and the annular skirt of the blocking element to place in communication, at the moment of injection, the interior of the reservoir with the injection needle.

The annular skirt 21 is provided with an annular lip 28 which serves as a piston segment during the injection phase and which contributes towards assuring the maintenance in position of the blocking element during the storage phase. Neck 18 and the interior of reservoir 10 have substantially the same diameter. The annular lip 28 has a diameter such that it is slightly compressed during the said storage phase, in a manner so as to avoid the risks of a permanent deformation of this lip as a result of a strong compression during a relatively long period.

The piston head 22 is dimensioned such that it is strongly compressed at the level of the constriction 17 to assure a perfect sealing of the reservoir during the storage phase. In its relaxed state, its diameter is however less than the interior diameter of the reservoir to allow for the passage of the medicine to be injected towards the transverse arm 27 of the central conduit during the injection phase.

Along the length of its free end, the annular skirt 21 comprises a pad 29 which serves as an abutment stop by cooperating with the conical ramp converging towards the constriction 17 and defining the exact position of the blocking element at the moment of the bubble removal phase preceding the injection phase.

The needle protector 15 is fitted on one edge 30 provided at the base of the capsule, coaxially to the needle-carrier tip. It is preferably made integral with this capsule by means of a label 31, carrying various inscriptions allowing particularly for the identification of the medication to be injected or of the formulas for use and comprising a zone of reduced resistance at the junction point between the needle carrier and the capsule.

Cap 16 is fitted on a small collar 32 provided at the end of the capsule, coaxially to the reservoir. It comprises removable linkage means 33 which make it integral with wings 34 which are themselves integral with an annular edge 35 provided around the upper end of capsule 13. These removable linkage means 33 comprise a base 36 connected to cap 10 by means of a continuous annular element 37 or by means of discontinuous flaps which extend laterally around this cap and constitute a zone of reduced resistance, adapted to be broken by the user. The base 36 has a generally cylindrical or conical shape, whose smallest diameter is greater than the exterior diameter of the cap 16 preferably having a generally cylindrical shape. This base preferably has a shape which makes it possible to nest in an appropriate opening provided in the wings 34 and to be welded, preferably by ultrasound, to these wings.

The label 31 on the one hand and the removable linkage means 33 on the other hand guarantee the impenetrability and sealing of the enclosure which encloses the functional elements of the syringe during storage and constituted by the capsule 13 which nests in the needle protector 15 and the cap 16.

The use of the syringe described above necessitates a very simple preparatory phase which avoids any direct manipulation of the medicine, and, consequently, totally eliminates any risk of error and of contamination. This preparatory phase consists first of turning the syringe such that needle 14 points upwardly and the air or gas volume 38 on top of liquid medicine 11 contained in reservoir 10 is brought into contact with the piston head 22. The syringe being maintained in this position, the operator exerts an axial force, preferably by means of the thumb, on the end of the cap 16 while maintaining the syringe in its position, by wings 34, preferably by means of the index and of the pointer finger of the same hand. This force first has an effect to break the linkage between the cap 16 and base 36 at the level of the zone of reduced resistance defined by the annular element 37. It then has as consequence a relative displacement of the reservoir 10 and of the blocking element, this relative displacement making it possible to bring the opening of the transverse arm 27 of the central conduit beyond the constriction 17 within the reservoir 10. In effect, the cap 16 comprises support elements 39 provided at its bottom or on its interior lateral walls which are adapted to be supported against the exterior surface of the bottom of the cap 16. As a result, the displacement of the cap 16 with respect to the capsule 13 induces a relative displacement of the reservoir 10 and of the blocking element, the first being rendered integral with the cap 16 by the support elements 39 and the second being integral with the cap 13. The amplitude of this relative displacement is equal to the distance d which separates the end of the cap or the zone of reduced resistance 37 adjacent to this end and the annular surface 40 of the annular edge 35 of the capsule 13.

This position is shown by FIG. 2. The distance d is sufficient to drive the piston head 22 within reservoir 10 for on the one hand entirely evacuating the gas 38 and on the other hand driving back a quantity of liquid medication 11 sufficient to totally fill the interior conduit and to appear in the form of a first drop at the end of needle 14. In this way one obtains a complete bubble removal in the syringe which is thus ready for use.

From this moment the user can withdraw the cap 16 and proceed to the injection by progressively driving reservoir 10 into capsule 13, which serves to make the blocking element 12 penetrate which fills from this moment on the combined role of a piston and of a valve within this reservoir to push back the contents through the central conduit 26. To this end, the user can directly press on the end of the reservoir 10 for example by means of his thumb by retaining the syringe by its wings 34 by means of the index and the pointer finger. He can likewise use the needle protector 15 which may be equipped with interior abutments 41, which has been previously removed from the location where it is positioned during the storage phase and put in the place of cap 16. To withdraw the needle protector 15, it is indispensible to tear the linkage label 31 which, as previously mentioned, preferably comprises a zone of reduced resistance constituted for example by discontinuous notches positioned the length of a circular line.

The use of the needle protector to push the reservoir into the capsule is particularly advantageous when the reservoir comprises a double dose of medicine to be injected at different locations or at different times. In this case, the abutments 41 are defined in a manner such that the first half-dose is injected when the free end of the needle protector 15 is brought to rest against the annular surface 40 and the second half-dose is injected when the reservoir 10 is completely pressed down into the interior of capsule 13, i.e., when the piston head 22 rests against the bottom of the reservoir. It is understood that the injection of the second half-dose can only occur after the preliminary retraction of the needle protector 15.

As previously noted, the cap 16 serves to overcome the resistances and constraints which initially oppose displacement of the blocking element towards the interior of the reservoir, without risking spraying of the medicine in an uncontrolled manner outside of the syringe. The initial inertia is all that much greater when the tightening of the blocking element against the walls of the reservoir and more particularly against the walls of the neck of this reservoir is more substantial. Yet to assure a proper sealing of the reservoir during the storage phase which can be more or less long, it is useful that the tightening be as substantial as possible. Furthermoree, there exists within the reservoir a particularly useful excess pressure for the preservation of the medication. This excess pressure can, in certain cases, be exclusively induced during the positioning of the blocking element, which serves to reduce the interior volume of the reservoir and, consequently, to compress the atmosphere which caps the medicated liquid. It can likewise, in other cases, be due to the sum of this induced excess pressure and excess pressure caused by known technical means either during, or after the filling of the syringe. The combined effect of these various constraints creates a resistance which must be overcome and that the apparatus makes it possible to overcome with precision and without risk.

The use of this apparatus, while facilitating the manipulations, makes it possible to normalize the bubble removal by rendering it quasi-automatic and by guaranteeing its result. Furthermore, one can affirm that it indirectly allows for the storage of the medicine under excess pressure in the reservoir, which serves to improve the sealing of this reservoir by increasing the tightening between the neck and the blocking element, and, consequently, to increase the time of preservation of the medicine in the syringe.

Figure 3:
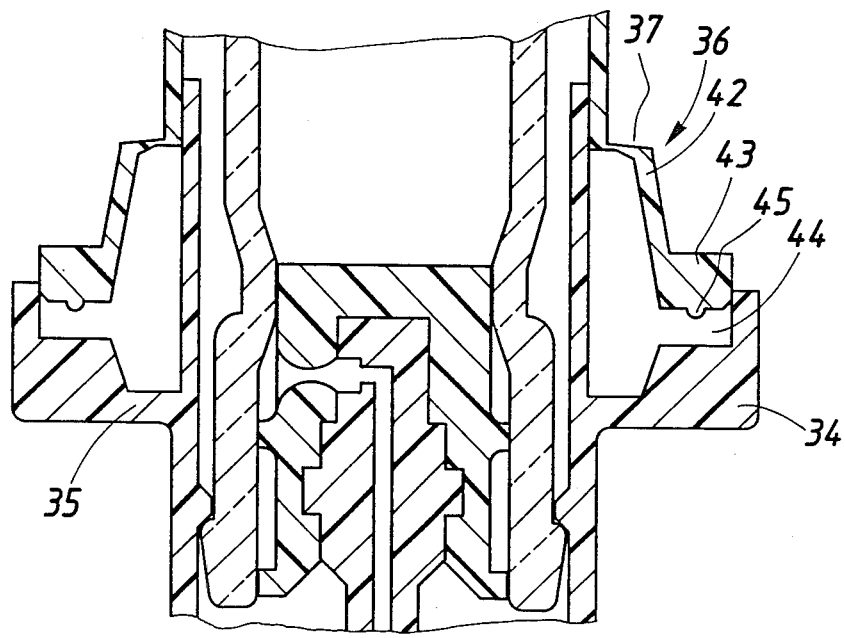
FIG. 3 illustrates a partial view, in longitudinal cross-section and magnified, of a detail of the syringe of the preceding drawings.

FIG. 3 shows in greater detail base 36 and its mode of attachment to the wings 34. Base 36 is composed of a central truncated conical zone 42 which connects between them on the one hand the annular element 37 which constitutes the zone of reduced resistance and an annular sole 43 adapted to nest n an opening 44 provided in the annular edge carrying the wings 34. The annular sole 43 comprises an annular protuberance 45 which is in fact a pad of material adapted to allow for ultrasonic welding, by application of a sonic electrode, of the base and the wings. The weld obtained is sufficiently resistant such that the rupture of the removable linkage means between the cap 16 and the capsule 13 occurs at the level of the zone of reduced resistance and not at the level of the welded zone.

The present invention is not limited to the embodiments described and illustrated by the figures but can undergo various modifications and assume various obvious alternatives for one of skill in the art.

We claim:

1. A prefilled syringe comprising an elongated reservoir having an open end and a closed end, said elongated reservoir adapted to contain a liquid to be injected, an injection element which is movable with respect to said reservoir, said injection element including a blocking member which is positioned within said reservoir, said blocking member comprising means for blocking said reservoir when said syringe is in a first, storage position, and comprising means for evacuating liquid from said reservoir when said syringe is in a second, injection position in which, liquid is adapted to be evacuated from said reservoir by said injection element, a capsule which is integrally connected to said blocking element, said capsule being mounted on said reservoir wherein at least one portion of said reservoir, adjacent to said open end of said reservoir, is engaged by said capsule, said prefilled syringe further comprising a cap which is positioned over said closed end of said elongated reservoir, said cap including means for detachably and integrally connecting said cap to said capsule when said syringe is in said first position, said capsule further comprising support means for allowing limited relative displacement between said movable injection element and said reservoir to effect movement of said syringe between said first and second syringe positions, wherein said connecting means comprises a cap base portion which is attached to said capsule by a reduced resistance zone of said cap.

2. A syringe in accordance with claim 1, wherein said cap base portion is attached to an annular edge of said capsule substantially adjacent to said at least one reservoir portion where said capsule is mounted on said reservoir.

3. A syringe in accordance with claim 2, wherein said annular edge comprises at least two lateral wings for engaging said cap base portion.

4. A syringe in accordance with claim 2, wherein said base portion is ultrasonically welded to said annular edge.

5. A syringe in accordance with claim 1, wherein said cap base portion has a generally conical configuration with a relatively small diameter portion which is larger than the exterior diameter of a main cap portion, said main cap portion having a generally cylindrical configuration.

6. A syringe in accordance with claim 5, wherein said reduced resistance zone comprises an annular section having a surface which extends laterally about the exterior of said cap.

7. A syringe in accordance with claim 5, wherein said reduced resistance zone comprises a flap assembly which extends laterally about the exterior of said cap.

8. A syringe in accordance with claim 1, said cap including at least one interior support element adapted to abut said closed reservoir end.

9. A prefilled syringe comprising an elongated reservoir having an open end and a closed end, said elongated reservoir adapted to contain a liquid to be injected, an injection element which is movable wih respect to said reservoir, said injection element including a blocking member which is positioned within said reservoir, said blocking member comprising means for blocking said reservoir when said syringe is in a first, storage position, and comprising means for evacuating liquid from said reservoir when said syringe is in a second, injection position in which liquid is adapted to be evacuated from said reservoir by said injection element, a capsule which is integrally connected to said blocking element, said capsule being mounted on said reservoir wherein at least one portion of said reservoir, adjacent to said open end of said reservoir, is engaged by said capsule, said prefilled syringe further comprising a cap which is positioned over said closed end of said elongated reservoir, said cap including means for detachably and integrally connecting said cap to said capsule when said syringe is in said first position, said capsule further comprising support means for allowing limited relative displacement between said movable injection element and said reservoir to effect movement of said syringe between said first and second syringe positions, wherein said support means comprises at least one abutment adapted to engage an edge of said cap when said syringe is in said second syringe position, each said abutment and said edge being spaced from each other, when said syringe is in said first syringe position, by a distance (d) which is substantially equal to the extent of said limited relative displacement between said movable injection element and said reservoir.

10. A syringe in accordance with claim 9, wherein said abutment comprises a surface of said annular capsule edge, said annular capsule edge being connected to said cap base by a reduced resistance zone.

11. A prefilled syringe comprising an elongated reservoir having an open end and a closed end, said elongated reservoir adapted to contain a liquid to be injected, an injection element which is movable with respect to said reservoir, said injection element including a blocking member which is positioned within said reservoir, said blocking member comprising means for blocking said reservoir when said syringe is in a first, storage position, and comprising means for evacuating liquid from said reservoir when said syringe is in a second, injection position in which liquid is adapted to be evacuated from said reservoir by said injection element, a capsule which is integrally connected to said blocking element, said capsule being mounted on said reservoir wherein at least one portion of said reservoir, adjacent to said open end of said reservoir, is engaged by said capsule, said prefilled syringe further comprising a cap which is positioned over said closed end of said elongated reservoir, said cap including means for detachably and integrally connecting said cap to said capsule when said syringe is in said first position, said capsule further comprising support means for allowing limited relative displacement between said movable injection element and said reservoir to effect movement of said syringe between said first and second syringe positions, said syringe further comprising means for protecting a needle attached to said injection element, said protecting means including abutments which comprise means for limiting the relative displacement of said reservoir and said blocking element, said abutments being positioned so that the extent of said relative displacement corresponds to the amount of movement of said injection element is necessary in order to inject a half dose of liquid from said reservoir.

12. A prefilled syringe comprising an elongated reservoir having an open end and a closed end, said elongated reservoir adapted to contain a liquid to be injected, an injection element which is movable with respect to said reservoir, said injection element including a blocking member which is positioned within said reservoir, said blocking member comprising means for blocking said reservoir when said syringe is in a first, storage position, and comprising means for evacuating liquid from said reservoir when said syringe is in a second, injection position in which liquid is adapted to be evacuated from said reservoir by said injection element, a capsule which is integrally connected to said blocking element, said capsule being mounted on said reservoir wherein at least one portion of said reservoir, adjacent to said open end of said reservoir, is engaged by said capsule, said prefilled syringe further comprising a cap which is positioned over said closed end of said elongated reservoir, said cap including means for detachably and integrally connecting said cap to said capsule when said syringe is in said first position, said capsule further comprising support means for allowing limited relative displacement between said movable injection element and said reservoir to effect movement of said syringe between said first and second syringe positions, wherein said connecting means comprises a frangible area for separating said capsule from said cap so as to permit relative movement therebetween.

13. A prefilled syringe in accordance with claim 12, wherein said blocking element is connected to a piston having a central bore, said central bore comprising means for fluidically connecting the interior of said reservoir to a needle which is attached to of said bore.

* * * * *

UNITED STATES PATENT AND TRADEMARK OFFICE
CERTIFICATE OF CORRECTION

PATENT NO. : 4,772,271
DATED : September 20, 1988
INVENTOR(S) : Gabriel MEYER et al.

It is certified that error appears in the above-identified patent and that said Letters Patent is hereby corrected as shown below:

At column 5, line 14, change "Furthermoree" to ---Furthermore---.

At column 5, line 44, change "n" to ---in--- after "nest".

Signed and Sealed this

Twentieth Day of March, 1990

Attest:

JEFFREY M. SAMUELS

Attesting Officer

Acting Commissioner of Patents and Trademarks